United States Patent
Schilp et al.

(10) Patent No.: US 10,056,071 B2
(45) Date of Patent: Aug. 21, 2018

(54) DEVICE FOR INSPECTING WORKPIECE SURFACES AND STRIP MATERIALS

(71) Applicant: ZS-HANDLING GMBH, Regensburg (DE)

(72) Inventors: Michael Schilp, Garching (DE); Josef Zimmermann, Regensburg (DE); Adolf Zitzmann, Teunz (DE)

(73) Assignee: ZS-Handling GmbH, Regensburg (DE)

( * ) Notice: Subject to any disclaimer, the term of this patent is extended or adjusted under 35 U.S.C. 154(b) by 28 days.

(21) Appl. No.: 14/906,793

(22) PCT Filed: Jul. 22, 2014

(86) PCT No.: PCT/DE2014/000375
§ 371 (c)(1),
(2) Date: May 2, 2016

(87) PCT Pub. No.: WO2015/010681
PCT Pub. Date: Jan. 29, 2015

(65) Prior Publication Data
US 2016/0260424 A1    Sep. 8, 2016

(30) Foreign Application Priority Data

Jul. 22, 2013 (DE) .................... 10 2013 012 174

(51) Int. Cl.
*G10K 15/00* (2006.01)
*G01N 21/89* (2006.01)
(Continued)

(52) U.S. Cl.
CPC .......... *G10K 15/00* (2013.01); *F16C 32/0603* (2013.01); *G01B 7/10* (2013.01);
(Continued)

(58) Field of Classification Search
CPC ....... G10K 15/00; F16C 32/0603; G01B 7/10; G01B 11/06; G01N 21/84; G01N 27/72; G01N 21/8901
See application file for complete search history.

(56) References Cited

U.S. PATENT DOCUMENTS 5,036,944 A * 8/1991 Danley .................. G10K 15/00
                                                            181/0.5
6,455,982 B1 * 9/2002 Hashimoto .......... B65G 35/005
                                                            310/328
(Continued)

FOREIGN PATENT DOCUMENTS

DE      199 09 534      9/2000
EP      0 315 315       5/1989
(Continued)

OTHER PUBLICATIONS

International Search Report issued by the European Patent Office in International Application PCT/DE2014/000375.

*Primary Examiner* — Francis Gray
(74) *Attorney, Agent, or Firm* — Henry M. Feiereisen LLC

(57) ABSTRACT

A device for inspecting a workpiece surface includes a sensor, a sonotrode having a sound-emitting surface and rigidly connected to the sensor to form a sensor unit, and a movable positioning device coupled with the sensor unit to position the sensor unit in a position opposite to the workpiece surface. The positioning device includes a force-applying member to urge the sensor unit in a direction of the workpiece or strip material surface by applying a predefined urging force or using gravity as the urging force. The sound-emitting surface of the sonotrode generates ultrasonic oscillations to produce an ultrasonic levitation force field in the presence of a gaseous medium between the workpiece surface and the sound-emitting surface to thereby generate a (Continued)

counterforce in opposition to the urging force so that the sensor unit is held hovering at a distance to the workpiece or strip surface.

5 Claims, 2 Drawing Sheets

(51) Int. Cl.
*F16C 32/06* (2006.01)
*G01B 7/06* (2006.01)
*G01B 11/06* (2006.01)
*G01N 21/84* (2006.01)
*G01N 27/72* (2006.01)

(52) U.S. Cl.
CPC ............ *G01B 11/06* (2013.01); *G01N 21/84* (2013.01); *G01N 21/8901* (2013.01); *G01N 27/72* (2013.01)

(56) References Cited

U.S. PATENT DOCUMENTS

| | | | |
|---|---|---|---|
| 7,260,449 B2 | 8/2007 | Zimmermann et al. | |
| 7,870,946 B2 | 1/2011 | Zimmermann et al. | |
| 8,794,877 B2 | 8/2014 | Schilp et al. | |
| 8,836,933 B2 | 9/2014 | Schilp et al. | |
| 2012/0274011 A1 | 11/2012 | Schilp et al. | |
| 2012/0327402 A1 | 12/2012 | Schilp et al. | |
| 2014/0041186 A1 | 2/2014 | Schilp et al. | |
| 2015/0015013 A1 | 1/2015 | Schilp et al. | |
| 2015/0290711 A1* | 10/2015 | Norfolk | B23K 20/103 425/78 |
| 2016/0163307 A1* | 6/2016 | Gstoettenbauer | G01B 5/0002 73/866.5 |
| 2016/0250728 A1* | 9/2016 | Schilp | B23K 26/361 118/500 |

FOREIGN PATENT DOCUMENTS

| | | |
|---|---|---|
| WO | WO 94/18643 | 8/1994 |
| WO | WO 01/23869 | 4/2001 |

* cited by examiner

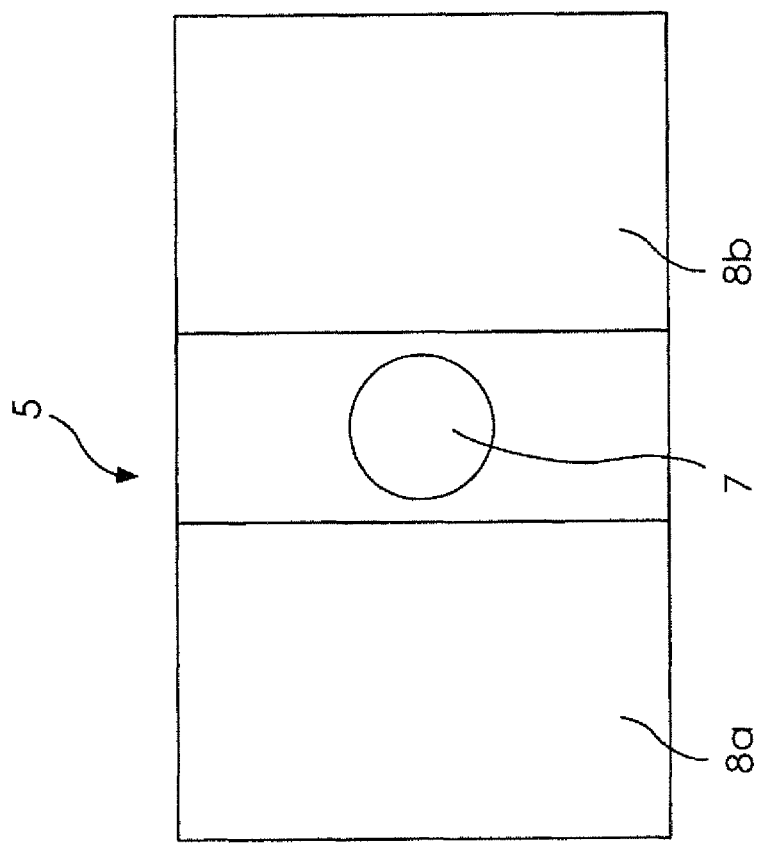

DEVICE FOR INSPECTING WORKPIECE SURFACES AND STRIP MATERIALS

CROSS-REFERENCES TO RELATED APPLICATIONS

This application is the U.S. National Stage of International Application No. PCT/DE2014/000375, filed Jul. 22, 2014, which designated the United States and has been published as International Publication No. WO 2015/010681 and which claims the priority of German Patent Application, Serial No. 20 2013 012 174.4, filed Jul. 22, 2013, pursuant to 35 U.S.C. 119(a)-(d).

BACKGROUND OF THE INVENTION

The invention relates to a device for the inspection of workpiece surfaces using a sensor, such as, e.g., a camera or an eddy current sensor. The invention relates in particular to a device which is suitable to hold the sensor at a constant distance to the workpiece surface and to rapidly correct a change in distance. The invention further relates to the inspection or measurement of material properties of strip materials.

Systems are known in the art to make it possible to inspect a surface of a workpiece or strip material. For this purpose, sensors must be kept precisely at a predetermined position. When, e.g., an optical inspection is to be executed by an optical system having a very shallow depth of field, the distance of the objective of this system and the workpiece surface must be kept constant as the optical system is guided across the workpiece surface. Such systems are known from the documents WO94/18643 and WO01/23869 A1. Comparable requirements apply also to other sensors and other measuring or inspection processes such as, e.g., for capacitive or inductive inspection processes.

As the required accuracy increases, the demands on the mechanical design of the measuring arrangement increase as well. This is especially true, when the measurement accuracy depends on the compliance with a defined distance between the sensor position and the workpiece surface. When, e.g., during monitoring of strip materials, a sensor is to be moved in close proximity across the surface of the strip material transversely to the direction of movement of the strip, rigid traverse bars are used for this purpose.

Since the strip material normally oscillates slightly during movement, measuring errors occur. Also, measuring errors are encountered, when the strip passes at the measurement position over a roller, because rollers can be out-of-round. When the strip material to be inspected involves, e.g. a steel sheet with a hard surface, the sensor may be coupled in such a case with a carriage which has a support wheel rolling on the surface of the steel strip, so that the sensor has the same distance to the steel strip surface at all times.

There are, however, a number of applications in which the strip material must be inspected during a treatment process, e.g. a coating process. The strip material passes hereby e.g. a drying tunnel in which a constant temperature and a uniform temperature distribution must be maintained. In this case, the afore-described device cannot be used for two reasons: As a result of the direct mechanical contact of the support wheel with the strip material, the sensitive surface of the strip material could be damaged, on one hand, and the surface temperature of the strip material could be altered at the contact point, on the other hand.

SUMMARY OF THE INVENTION

The object of the invention is therefore to provide a device with which a sensor can be positioned or moved at a precisely predefined distance above a moving workpiece surface and the distance between the measuring system and the workpiece surface, hereinafter referred to as measuring distance, is kept constant in the presence of deviations in thickness of the workpiece or out-of-roundness of a support or deflection roller. A further requirement is that readjustment of the sensor for maintaining the desired measuring distance has to be realized in very short times and that the temperature distribution of the strip material is affected as little as possible at the measuring point.

The object is achieved in accordance with the invention by a device for the inspection of workpiece surfaces and strip materials, which device includes at least one sensor, which is configured for the inspection of a particular workpiece surface and or a particular strip material, at least one sonotrode having a sound-emitting surface and connected mechanically rigidly to the sensor to form a sensor unit, and a movable positioning device coupled with the sensor unit for positioning the sensor unit in a position opposite to the workpiece or strip surface, wherein the positioning device includes a force-applying member to urge the sensor unit in the direction of the workpiece surface, wherein either a predefined urging force or the gravity is used as the urging force, wherein the sound-emitting surface of the sonotrode executes ultrasonic oscillations so that an ultrasonic levitation force field acts in the presence of a gaseous medium between the workpiece or strip surface and the sound-emitting surface to generate a counterforce in opposition to the urging force so that the sensor unit is held hovering at a distance to the workpiece or strip surface, wherein the sensor is configured to detect surface structure deviations or color deviations or deviations of the reflection behavior or material inhomogeneities or defects of the workpiece surface or the strip, or the strip thickness or the thickness of applied coatings, or the surface temperature on the workpiece or strip surface.

The present invention resolves prior art shortcomings by mechanically coupling at least one ultrasonic sonotrode with the measuring system. The ultrasonic sonotrode is oriented such that its sound-emitting surface lies opposite to the workpiece surface and is operated such that the emitted sound waves produce a levitation force field which prevents contact of the sonotrode surface with the workpiece surface, when the sonotrode and the workpiece are urged against each other by a force-applying member.

A force-applying member is to be understood as relating to all technical means which are suitable to urge the sonotrode with the attached sensor by a predetermined urging force against the workpiece surface. The urging force may be realized by a mechanical spring, by a controlled mechanical drive, a hydraulic drive, or a pneumatic drive. An urging force can also be generated through magnetic attraction or repulsion, also through use of gravitational force upon a mass or by vacuum, i.e. by using the external air pressure.

An important advantage of the afore-described device for surface inspection resides in that the levitation force field does not significantly affect the temperature distribution at the measurement or inspection site.

The distance of the sensor from the workpiece surface may, optionally, be changed by varying the electrical power consumption of the sonotrode. As a result, the vibration amplitude changes. Likewise, the electric power control of the sonotrode enables a very rapid change in the distance of the sensor from the workpiece surface.

The sound-emitting surface of the sonotrode has a shape in correspondence with the workpiece surface, i.e. it is flat when the workpiece surface is flat, in the case of two or three-dimensionally curved workpiece surface, it is curved complementary thereto.

According to another feature of the present invention, a distance control for controlling the distance between the workpiece surface and the work unit is provided, with the distance being variable through change of the sound energy. This results in a particularly fast and precise readjustment of the sensor with respect to the workpiece surface.

According to another feature of the present invention, the sensor is surrounded by at least two sonotrodes. This arrangement is particularly advantageous because the sensor is shielded from harmful influences.

According to another feature of the present invention, the sensor is coupled with at least two sonotrodes which can be activated separately. This embodiment has the advantage that the different activation of the sonotrodes enables also a slight tilt of the movably suspended sensor unit to thereby position the sensor even more accurately.

BRIEF DESCRIPTION OF THE DRAWING

An example of the device for surface inspection is explained in greater detail with reference to the drawings in which:

FIG. 2 is a schematic bottom view of a sensor unit accommodated in the tunnel kiln.

DETAILED DESCRIPTION OF PREFERRED EMBODIMENTS

Figure 1:
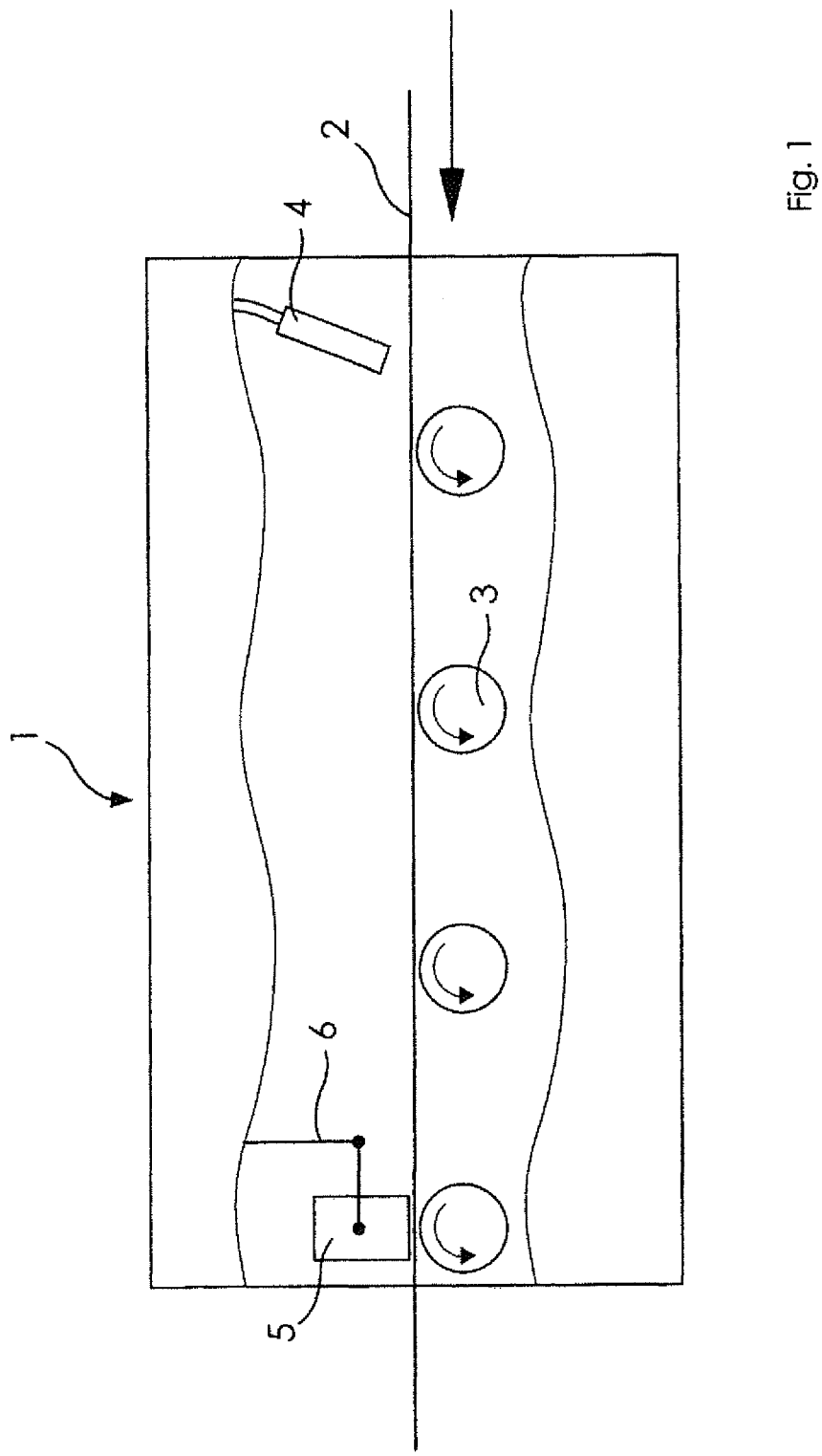
FIG. 1 is a schematic illustration of a tunnel kiln incorporating the subject matter of the present invention.

FIG. 1 shows a tunnel kiln 1, in which a heat treatment process is carried out. A strip material 2 is guided on driven rollers 3 through the tunnel kiln 1. At the entrance of the tunnel kiln 1, paint is sprayed onto the strip material 2 by a spray device 4. Arranged at the exit of the tunnel kiln 1 is a schematically illustrated sensor unit 5 for surface inspection. The sensor unit 5 is suspended on a movable suspension 6 and hovers at a distance of 300 µm above the strip material 2. It is to be noted that the distance of the sensor unit 5 in relation to the strip material surface is not adjusted by the movable suspension 6. The suspension 6 is merely intended to carry part of the weight of the sensor unit 5. The remaining part of the weight is used as gravimetric urging force which acts in opposition to a force which is generated by the ultrasonic levitation force field.

FIG. 2 schematically shows the bottom side of the sensor unit 5 that is directed towards the surface of the strip material 2. Reference numeral 7 designates a sensor, e.g. a camera. Reference numerals 8a, b designate two sonotrodes which produce an ultrasound levitation force field. It should be emphasized that the paint on the strip material 2 exiting the tunnel kiln has not yet cured and hence is still sensitive to mechanical contact. It is also of particular importance that the temperature of the strip is kept constant and is not affected by a measurement process. It is equally important to be able to determine the layer thickness immediately downstream of the spray device in order to be able to rapidly detect deviations in the paint thickness or other flaws and to correct them.

Since the levitation force field has almost no influence on the temperature distribution on the surface of the strip material 2, the measurement has no influence on the sensitive paint layer.

What is claimed is:

1. A device for the inspection of a workpiece surface or a strip material, comprising:
   at least one sensor;
   at least one sonotrode having a sound-emitting surface and connected mechanically rigidly to the sensor to form a sensor unit; and
   a movable positioning device coupled with the sensor unit and configured to position the sensor unit in a position opposite to the workpiece surface or a surface of the strip material, said positioning device including a force-applying member to urge the sensor unit in a direction of the workpiece or strip material surface by applying a predefined urging force or using gravity as the urging force,
   said sound-emitting surface of the sonotrode generating ultrasonic oscillations to produce an ultrasonic levitation force field in the presence of a gaseous medium between the workpiece or strip material surface and the sound-emitting surface to thereby generate a counter-force in opposition to the urging force so that the sensor unit is held hovering at a distance to the workpiece or strip surface.

2. The device of claim 1, wherein the sensor is configured for the inspection of the workpiece surface or the strip material by detecting surface structure deviations or color deviations or deviations of the reflection behavior or material inhomogeneities or defects of the workpiece surface or the strip material, or a strip thickness, or a thickness of applied coatings, or a surface temperature on the workpiece surface or surface of the strip material.

3. The device of claim 1, further comprising a distance control for controlling a distance between the workpiece surface and a work unit, with the distance being changed by changing a sound energy.

4. The device of claim 1, wherein the sensor is surrounded by at least two of said sonotrode.

5. The device of claim 1, wherein the sensor is coupled with at least two of said sonotrode, said two sonotrodes being configured so as to be controllable separately.

* * * * *